United States Patent [19]
Puritch et al.

[11] Patent Number: 5,700,473
[45] Date of Patent: Dec. 23, 1997

[54] TRIGLYCERIDE ENHANCED PYRETHRIN-BASED ARTHROPODICIDAL COMPOSITION

[75] Inventors: George S. Puritch, Saanichton; David S. Almond, Victoria; Diana L. Parker, Brentwood, all of Canada

[73] Assignee: W. Neudorff GmbH KG, Emmerthal, Germany

[21] Appl. No.: 519,047

[22] Filed: Aug. 24, 1995

[51] Int. Cl.⁶ .................................................. A01N 65/00
[52] U.S. Cl. ........................................................... 424/405
[58] Field of Search ............................................. 424/405

[56] References Cited

U.S. PATENT DOCUMENTS

| | | | |
|---|---|---|---|
| 2,087,028 | 7/1937 | Gnadinger | 167/24 |
| 2,104,757 | 1/1938 | O'Kane | 167/43 |
| 2,202,145 | 5/1940 | Eagleson | 167/24 |
| 2,463,324 | 3/1949 | Simanton | 167/24 |
| 2,726,188 | 12/1955 | Allison | 167/24 |
| 3,186,903 | 6/1965 | Soltes | 167/24 |
| 3,560,613 | 2/1971 | Miskus | 424/174 |
| 3,859,121 | 1/1975 | Yeadon et al. | 424/405 |
| 3,887,710 | 6/1975 | Shaver et al. | 424/300 |
| 4,617,318 | 10/1986 | Marei . | |
| 4,677,117 | 6/1987 | Haus | 514/461 |
| 4,983,591 | 1/1991 | Puritch et al. . | |
| 5,037,654 | 8/1991 | Puritch et al. | 424/405 |
| 5,242,907 | 9/1993 | Dawson . | |

FOREIGN PATENT DOCUMENTS

| | | |
|---|---|---|
| 991628 | 4/1944 | France . |
| 9013000 | 11/1991 | Germany . |
| 2 058 569 | 9/1980 | United Kingdom ........ A01N 25/22 |
| 2 095 109 | 3/1981 | United Kingdom ........ A01N 25/30 |

OTHER PUBLICATIONS

George S. Puritch et al., "Effect of Fatty Acid Salts on the Growth of *Botrytis Cinerea*" pp. 491–494, *Canadian Journal of Botany*, vol. 59, No. 4 (Apr. 1981).

A. Mallis, "Handbook of Pest Control", pp. 903–909, (Franzak and Foster Company) (1982).

M.F. Treacy et al., "Soybean and Cottonseed Oils as Adjuvants and Diluents for Insecticides used to Control Sorghum Midge", pp. 39–43, *The Southwestern Entomologist*, Suppl. No. 11 (Dec. 1986).

L.S. Hesler et al., "Uses of Oils in Insect Control", pp. 1–8, *The Southwestern Entomologist*, Suppl. No. 11 (Dec. 1986).

"Box C. Pyrethrum" Update, *The IPM Practitioner*, p. 7, vol. XV(1) 1993.

William Olkowski, "Natural and Synthetic Pryethrum Insecticides: Finding Your Way through the Maze", pp. 8–1 to 8–5, *Common Sense Pest Control*, V(1) (Winter 1989).

J. Grossman, "Horticultural Oils: New Summer uses on Ornamental Plan Pest", *The IPM Practitioner*, pp. 1–10, vol. XII, No. 8 (Aug. 1980).

Ahmed et al., *Phrethrum Post*, 13 (3), pp. 82–88 (1976).

*Primary Examiner*—Amy Hulina
*Attorney, Agent, or Firm*—Nutter, McClennen & Fish, LLP

[57] ABSTRACT

The pyrethrin-based nonphytotoxic arthropodicide is effective against a wide range of pests and is suitable for domestic and gardening uses. The composition comprises a triglyceride component derived from vegetable seed oils, a pyrethrum extract, and one or more surfactants. Optionally, antioxidants and emulsifiers may be added as well.

2 Claims, No Drawings

TRIGLYCERIDE ENHANCED PYRETHRIN-BASED ARTHROPODICIDAL COMPOSITION

BACKGROUND OF THE INVENTION

The present invention relates to non-phytotoxic, arthropodicidal compositions based on naturally occurring active ingredients. More particularly, the invention relates to pyrethrin-based arthropodicidal compositions.

In recent years, synthetic pesticides, including insecticides, have come under intense scrutiny due to the potential danger that they pose to humans and to other animals. Many such synthetic pesticides are also known to have long lasting deleterious environmental consequences. Because the risks associated with the use of synthetic pesticides often outweigh their advantages, significant research efforts have focused on naturally occurring compounds as pesticidal active ingredients.

The term "pyrethrum" is used to identify flower extracts that have long been known to possess insecticidal activity. Pyrethrums generally include the oleoresins of *Chrysanthemum cinerariaefolium*. These oleoresins contain several esters that are very effective insecticides against a wide range of insect pests. These esters, collectively called pyrethrins, are the most common botanical pesticides in the lawn and garden pesticide market. The pyrethrins are contact insecticides, causing rapid knockdown and mortality of insects at very low concentrations. As botanical products, these compounds are rapidly degraded through ultraviolet action on the pyrethrin molecules. In addition, the pyrethrins are quickly biodegraded by microorganisms. These features, combined with a relatively safe toxicological profile, have contributed to their commercial success against synthetic hydrocarbon-based pesticides.

The molecular structure of the pyrethrin esters has been used by many different companies to develop synthetic compounds. These synthetic compounds, called pyrethroids, are not naturally occurring and have chemical structures that differ from those of pyrethrins. Pyrethroids do, however, have the high contact effect of the natural pyrethrins. Pyrethroid compounds have a variety of configurations, and are marketed under a wide variety of brand names such as PERMETHRIN, CYPERMETHRIN, and RESMETHRIN. Many of the pyrethroids have been designed to last for a long time in the environment and thus give longer residual action. Despite their initial success, the pyrethroids have encountered insect resistance, after only a few years of use, which has limited their usefulness.

The natural pyrethrins, however, have remained popular and are commonly used in a variety of formulations. Usually, pyrethrins are combined with a variety of substances, called synergists, that enhance their effectiveness. One of the earliest of these synergists was sesame oil which contains the extractives sesamin and sesamolin (Casida, *Pyrethrum, The Natural Insecticide*, p. 329, Academic Press 1973). U.S. Pat. No. 2,463,324 (column 3, lines 1–9) teaches that it is the sesame oil extractives, not the oil itself, that are responsible for the enhanced activity of pyrethrins.

Subsequent research has led to the discovery of piperonyl butoxide (PBO), a mixture of 3,4- dioxymethylene-6-propyl benzyl butyl diethylene glycol ether and piperonyl cyclonene. This synergist is widely used in pyrethrin formulations. PBO is also sold separately as an insecticide. Recently, PBO has aroused controversy due to its potentially adverse effect on human liver enzymes responsible for degrading pesticides, and possible implications as a carcinogen (Olkowski, *Common Sense Pest Control* V(1), Winter 1989). Concerns such as these give rise to a need for alternative pyrethrin-based insecticidal composites which are free of PBO and other harmful additives.

One alternative approach to synergize pyrethrins uses specific fatty acid salts in combination with pyrethrins as described in U.S. Pat. No. 4,983,591 (Puritch et at.). Generally, pyrethrins are degraded in an alkaline environment and are, therefore, incompatible with fatty acid salts. However, this drawback was overcome by adjusting the pH of the aqueous mixture.

Accordingly, there is a need for new, naturally-based arthropodicidal compositions, and particularly those that represent enhanced pyrethrin-based formulations.

It is thus an object of the invention to provide new and effective arthropodicidal formulations based on naturally occurring ingredients. Another object is to provide a pyrethrin-based arthropodicidal formulation that is free of potentially harmful synergists or additives. A further object is to provide an environmentally safe arthropodicidal formulation that is effective against a range of garden and household pests, without exhibiting any significant levels of phytotoxicity. Yet another object is to provide a new and effective formulation that is active against ants and caterpillars. These and other objects will be apparent to those having ordinary skill in the art upon reading the disclosure that follows.

SUMMARY OF THE INVENTION

The invention provides an effective arthropodicidal formulation that includes naturally occurring active ingredients. The arthropodicidal formulation is effective against the variety of household and garden pests. It is a particularly useful formulation when used to combat ants and leaf-eating caterpillars. The composition further exhibits little or no phytotoxicity and thus can be freely applied to plants and flowers. Moreover, it poses few, if any, health risks to humans or animals and thus can be used in and around dwellings.

The arthropodicidal composition of the invention comprises as active ingredients naturally occurring pyrethrins, derived from a pyrethrum extract. The composition also includes triglycerides derived from vegetable seed oils, wherein the triglycerides have one or more saturated or unsaturated fatty acids with 14 to 24 carbon atoms. Preferably, about 70% or more of the fatty acids of the triglycerides are unsaturated fatty acids. In a preferred embodiment the triglyceride component is free of non-triglyceride seed oil components or other additives or components that contribute to phytotoxicity, or which would pose health hazards to humans or other animals. The formulation also includes surfactants to improve the processability and stability of the formulation. Preferably, the surfactants are non-ionic surfactants selected from the group consisting of ethoxylated sorbitan derivatives, ethoxylated fatty acids, and mixtures thereof.

The triglyceride component at least serves as an adjuvant and in some instances also serves as a co-active ingredient. The triglyceride component even helps to achieve a synergistic effect against some pests. An additional advantage of the triglyceride component is that it serves as a carrier within which the pyrethrins can be solubilized.

The composition is particularly effective against ants and leaf-eating caterpillars in that the pyrethrin component and the triglyceride component combine to achieve a dramatic synergistic effect against such pests.

The composition can be prepared in concentrated formulations, which can be diluted with water, or in ready-to-use formulations.

DETAILED DESCRIPTION OF THE INVENTION

The arthropodicidal composition of the invention comprises one or more pyrethrin active ingredients that are derived from a pyrethrum extract. The composition also includes a triglyceride component that is derived from vegetable seed oils, within which the pyrethrins can be solubilized. The triglyceride component at least serves as an adjuvant, and in some instances acts as a co-active ingredient. A synergistic effect can even be achieved against some pests.

The triglyceride component preferably is derived from vegetable seed oils and has triglycerides with one or more saturated or unsaturated fatty acids with 14 to 24 carbon atoms. Preferably, 70% or more of the fatty acids are unsaturated. Further, the triglyceride component should be in the form of triglycerides that are free of other seed oil components or additives that may contribute to phytotoxicity, or those that are potentially dangerous to humans and other animals. The composition should also be free of any component that reduces the efficacy of the product. The composition further includes a surfactant component which contributes to formulation processing and formulation stability. Optionally, an antioxidant can be used to enhance environmental stability of the composition, and stabilizers can be used to improve formulation stability and to improve processability.

Pyrethrum extracts are naturally occurring plant products that are obtained from dried flowers, such as chrysanthemum (*Chrysanthemum cinerariaefolium*). The principal parts of the flower from which pyrethrum extracts are derived include the achenes, petals, receptacles, scales, and disc florets. Pyrethrum extracts are commercially available from a number of sources, including the Pyrethrum Marketing Board, Kenya, Africa; M.G.K. Company, Minneapolis Minn.; Fairfield American Corp., Rutherford, N.J.; and Prentiss Drug and Chemical Co., Floral Park, N.Y.

The active agents of pyrethrum extracts are generally referred to as "pyrethrins." Known pyrethrins include pyrethrin I, pyrethrin II, cinerin I, cinerin II, jasmolin I, and jasmolin II. The total pyrethrin component of commercially available pyrethrum extracts typically is in the range of about 15 to 30% by weight. More commonly, pyrethrum extracts are utilized with a total pyrethrin content in the range of about 20 to 25% by weight.

The triglyceride component, as noted above, preferably is one that is obtained from vegetable seed oils and which contains almost exclusively triglycerides having one or more saturated or unsaturated fatty acids with 14 to 24 carbon atoms. Preferably, at least 70% of the fatty acids are unsaturated. This component should be refined and free of compounds or constituents such as seed extract by-products including terpenes and the like that could contribute to phytotoxicity. Other compounds that pose environmental or health risks, such as piperonyl butoxide (PBO) should also be absent from the component.

Preferred sources of the triglyceride component include commercially available vegetable seed oils such as canola oil, corn oil, soybean oil, sunflower oil, cottonseed oil, rape seed oil, safflower oil, peanut oil, and olive oil.

Non-ionic surfactants are a preferred class of surfactants that are useful in the composition of the present invention. Preferred nonionic surfactants include ethoxylated sorbitan derivatives, ethoxylated fatty acids, and mixtures thereof. Exemplary ethoxylated sorbitan derivatives include TWEEN surfactants, available from ICI Americas, Inc., Agricultural Products Division, Wilmington, Del., such as TWEEN 81 and TWEEN 85. Other suitable sorbitan derivatives include EMSORB 6903 and EMSORB 6913, available from Henkel Corp., Cincinnati, Ohio. Suitable ethoxylated fatty acids include CHEMAX T09 and CHEMAX E400MO available from Chemax, Inc., Greenville, S.C., and ALKASURF 014 and ALKASURF 09, available from Rhone Poulenc, Cranberry, N.J.

Antioxidants can be useful additives for the composition in order to reduce the effect of oxidation of the pyrethrins. Examples of suitable antioxidants include butylated hydroxytoluene (BHT), butylated hydroxy anisole (BHA), α-tochopherol, and 2,6-dioctadecyl-P-cresol (DOPC).

Additional additives, such as stabilizers, may desirably be added to improve the stability and shelf life of the composition. Examples of suitable additives include gum arabic, guar gum, sodium caseinate, polyvinyl alcohol, locust bean gum, xanthan gum, kelgum, and mixtures thereof.

The pyrethrin active ingredients, as noted above, are present at a pesticidally active concentration. Preferably, the pyrethrins are present at a level of between about 20 and 20,000 ppm. More preferably, the pyrethrins are present at between about 50 and 4000 ppm. Generally, pyrethrins possess acceptable pesticidal activity in applied concentrations in the range of about 50 to 150 ppm. Higher than necessary concentrations of pyrethrins may be applied (i.e., concentrations in the range of about 150 to 4000 ppm) where a residual or longer lasting pesticidal effect is desired. Concentrated formulations obviously have higher levels of pyrethrins (i.e., about 2500 to 200,000 ppm), but are typically diluted prior to use.

The triglyceride component serves as a carrier within which the pyrethrins are solubilized. The triglyceride component is also believed to enhance the activity and effect of the pyrethrins by enabling the pyrethrins to penetrate into the bodies of the pests. To some extent the triglycerides also contribute some degree of arthropodicidal activity, and the composition is able to achieve a synergistic effect against some pests. The triglyceride component may be present in applied compositions at a concentration in the range of about 1 to 5% by weight. Concentrated formulations typically contain as much as about 85 to 98% by weight of the triglyceride component.

Surfactants are also useful to the pesticidal composition of the invention as they improve the stability and the ease of processing the formulation. The total concentration of surfactants present within the formulation preferably is in the range of about 0.05 to 1.0% by weight of an applied composition. Concentrated formulations may obviously include a higher level of surfactants, preferably in the range of about 2–10% by weight.

Antioxidants or other such formulation stabilizers or enhancers may be present in relatively low mounts in an applied form of the compositions. Typically antioxidants are present at about 50 to 500 ppm of the composition. Similarly, applied compositions may have 50 ppm to 0.2% by weight of other additives such as stabilizers.

The insecticidal composition of the invention can be prepared in various forms, including sprayable liquids and aerosols. A sprayable liquid form is preferred. Liquid compositions may be prepared in a concentrated form or in a ready-to-use form. A concentrated formulation is primarily a triglyceride-based emulsifiable composition in which the triglyceride component is believed to contribute some level of activity, and is also a solvent and a carrier for the pyrethrins. This composition can be diluted with water before application. Ready-to-use formulations are stable aqueous emulsions in which water is the primary ingredient, yet the pyrethrin and triglyceride components are present at sufficient concentrations to provide arthropodicidal activity.

Exemplary concentrated formulations include about 85 to 98% by weight of one or more triglycerides from vegetable seed oil component, about 1 to 4% by weight of pyrethrum extract (with 25% active pyrethrins), and about 2–10% by weight of a surfactant component. The triglyceride component preferably consists of triglycerides having one or more saturated or unsaturated fatty acids with between 14 and 24 carbon atoms. Preferably, the triglyceride component is derived from a vegetable seed oil such as canola oil, cottonseed oil, corn oil, rape seed oil, soybean oil, sunflower oil, safflower oil, peanut oil, olive oil, or mixtures thereof.

The pyrethrum extract, as noted above, is commercially available in a form that contains 25% active pyrethrins.

The surfactant may be one or a mixture of ethoxylated sorbitan derivatives, ethoxylated fatty acids, or mixtures thereof. Among the preferred surfactants are TWEEN 81, TWEEN 85, EMSORB 6903, EMSORB 6913, ALKASURF 014, ALKASURF 09, CHEMAX T09, and CHEMAX E400MO.

Exemplary concentrated formulations are shown below:

| %    | Component |
|------|-----------|
|      | Formulation A |
| 90.0 | Triglycerides from canola oil |
| 2.0  | Pyrethrum extract with 25.0% active pyrethrins |
| 5.0  | TWEEN 81 |
| 3.0  | EMSORB 6903 |
|      | Formulation B |
| 90.0 | Triglycerides from soybean oil |
| 2.0  | Pyrethrum extract with 25.0% active pyrethrins |
| 5.0  | TWEEN 81 |
| 3.0  | EMSORB 6903 |
|      | Formulation C |
| 94.0 | Triglycerides from canola oil |
| 2.0  | Pyrethrum extract with 25.0% active pyrethrins |
| 4.0  | Chemax T09 |

Ready-to-use formulations typically are aqueous emulsions that may be used as packaged, without dilution. Many aqueous pyrethrin formulations that must remain non-phytotoxic tend to degrade rapidly. However, the ready-to-use formulation of the present invention has been found to be stable in that it maintains a long shelf life and it maintains its arthropodicidal activity and non-phytotoxicity.

A ready-to-use formulation according to the present invention has approximately 1 to 5 by weight of the triglyceride component, which is as described above with respect to the concentrated formulation. Further, the active pyrethrins are present at about 20 to 4000 ppm. The ready-to-use formulation may optionally include an antioxidant which, if present, exists at quite small concentrations in the range of 50 ppm to 500 ppm. The total concentration of surfactant present in the ready to use formulation, which is described above with respect to the concentrated formulations, can be present at about 500 to 10000 ppm. Additionally, a stabilizer or emulsifying agent is also present in the ready-to-use formulation at a concentration in the range of 50 ppm to 1000 ppm.

The antioxidant preferably is a hydroxylated toluene. Preferred antioxidants included butylated hydroxytoluene (BHT) and butylated hydroxy anisole (BHA).

Useful stabilizers include various gums and/or polymeric alcohols such as polyvinyl alcohol. Preferred stabilizers include gum arabic, locust bean gum, xanthan gum, and guar gum.

Exemplary ready-to-use formulations are shown below.

| %       | Component |
|---------|-----------|
|         | Formulation D |
| 2.00    | Triglycerides from canola oil |
| 0.04    | Active pyrethrins |
| 0.01    | BHT |
| 0.16    | TWEEN 81 + EMSORB 6903 |
| 0.03    | Gum Arabic |
| 97.76   | Water |
|         | Formulation E |
| 2.00    | Triglycerides from canola oil |
| 0.01    | Active pyrethrins |
| 0.10    | EMSORB 6903 |
| 0.07    | TWEEN 81 |
| Balance | Water |
|         | Formulation F |
| 2.00    | Triglycerides from canola oil |
| 0.01    | Active pyrethrins |
| 0.07    | EMSORB 6903 |
| 1.00    | TWEEN 81 |
| Balance | Water |
|         | Formulation G |
| 1.2     | Pyrethrum extract |
| 2.0     | Triglycerides from rape seed oil |
| 0.4     | TWEEN 81 |
| 0.02    | Gum Arabic |
| 0.01    | BHT |
| 96.37   | Water |

Additional exemplary ready-to-use formulations can be prepared having 1.84% by weight triglyceride component, 100 ppm pyrethrum, 100 ppm BHT, and the additional components shown in Table A.

TABLE A

| Component   | FORMULATION |      |      |      |      |         |         |         |       |       |         |       |
|-------------|------|------|------|------|------|---------|---------|---------|-------|-------|---------|-------|
|             | 1    | 2    | 3    | 4    | 5    | 6       | 7       | 8       | 9     | 10    | 11      | 12    |
| TWEEN 81    | 0.5% | 0.5% | 0.2% | 0.2% | 0.2% | 1250 ppm | 1250 ppm | 1250 ppm | 0.16% | 0.16% | 1250 ppm | 0.16% |
| EMSORB 6903 | —    | —    | —    | —    | —    | 750 ppm  | 750 ppm  | 750 ppm  | —     | —     | 750 ppm  | —     |
| Gum arabic  | 0.1% | —    | 250  | —    | 100  | 200      | —        | —        | 250   | —     | —        | —     |

TABLE A-continued

| Component | \multicolumn{12}{c}{FORMULATION} | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Guar gum | — | 0.1% | ppm | — | ppm | ppm | — | — | ppm | — | — | — |
| Locust bean gum | — | — | — | 250 ppm | — | — | 120 ppm | — | — | 250 ppm | — | — |
| Xanthan gum | — | — | — | — | — | — | 30 ppm | — | — | — | — | — |
| Kelgum | — | — | — | — | — | — | — | — | — | — | 200 ppm | 250 ppm |
| Sodium caseinate | — | — | — | — | — | — | — | 1000 ppm | — | — | — | — |

Ready-to-use formulations can be prepared by adding all ingredients, except water, to the triglyceride component while stirring thoroughly. Thereafter, the triglyceride mixture is added to water while rapidly agitating.

The composition of the invention may be applied in areas that are infested with pests, including in domestic areas, garden areas and on or around trees and shrubs. The composition exhibits virtually no phytotoxicity and thus may be applied to a variety of plants, flowers, trees, shrubs, and grasses. Further, due to its lack of toxicity to humans and other animals, the composition may be applied in and around dwellings and other domestic areas.

The composition is effective against a wide range of chewing and sucking insects and mites. The composition is particularly effective and useful to combat mites (order Acari), ants (order Hymenoptera), caterpillars (order Lepidoptera), flies (order Diptera), fleas (order Siphonaptera), beetles (order Coleptera), aphids, white fly and mealy bugs (order Homoptera), bugs (order Hemiptera), thrips (order Thysanoptera), and silverfish (order Thysanura).

The following examples serve to further illustrate the invention:

EXAMPLE 1

The phytotoxicity of the pyrethrum-based arthropodicidal compositions of the present invention as compared to various other compositions was assessed. The arthropodicidal compositions of the invention evaluated are those identified above as Formulation E and Formulation F.

Potted radish and nasturtium were sprayed to run off with the treatment formulations identified below in Table 1, using hand held sprayers. After treatment, the plants were arranged in a block design on a greenhouse bench. Assessment was done 7 days after treatment using a scale of 1 to 10. Thereafter, the plants were resprayed and assessed 6 days later. Six replicates were used for each treatment. A score of 2.0 or higher indicates unacceptable phytotoxicity.

TABLE 1

Phytotoxicity Assessment Formulations on Nasturtium and Radish Plants

| | | Mean Damage Rating ± Standard Deviation | | | |
|---|---|---|---|---|---|
| | | First spray | | Second Spray | |
| | Treatment | nasturtium | radish | nasturtium | radish |
| 1 | Formulation E | 1.7 ± 0.6 | 0.7 ± 0.5 | 1.8 ± 0.4 | 1.9 ± 0.6 |
| 2. | Formulation F | 0.9 ± 0.5 | 0.8 ± 0.3 | 1.3 ± 0.5 | 0.6 ± 0.4 |
| 3. | 100.0% Schultz-Instant Insect Spray ® (200 ppm pyrethrin, 0.2% PBO) | 3.4 ± 0.7 | 3.8 ± 0.7 | 8.1 ± 0.8 | 4.8 ± 2.1 |
| 4. | 55.0% Schultz-Instant Insect Spray ® (110 ppm pyrethrin, 0.11% PBO) | 3.6 ± 1.2 | 4.4 ± 1.4 | 6.2 ± 2.4 | 3.9 ± 2.7 |
| 5. | 0.1% Spruzit ® (40.0 ppm pyrethrin, 160.0 ppm PBO) | 2.0 ± 0.3 | 2.4 ± 1.0 | 2.9 ± 0.6 | 2.9 ± 0.8 |
| 6. | distilled water | 0.5 ± 0.3 | 0.2 ± 0.3 | 0.2 ± 0.4 | 0.1 ± 0.2 |

EXAMPLE 2

Two-spotted mites, *Tetranychus urticae* Koch, were used to infest bean plants. Twenty-five mites were placed on each bean plant and allowed to settle for one day. The infested bean plants were then sprayed with a hand held sprayer until wetted. Plants were randomized in a block design on the laboratory bench.

The tested arthropodicidal composition that was evaluated was derived from a concentrated formulation containing 94% by weight triglycerides from canola oil, 2% pyrethrum extract containing 25% active pyrethrins, and 4% ALKASURF 014. Prior to application the concentrate was diluted to contain 1.0% by weight triglycerides from canola oil and 56 ppm active pyrethrins.

Mortality was assessed 48 hours after spraying by counting all living and dead mites on the plant. The data obtained are shown below in Table 2.

TABLE 2

Mortality of Two-Spotted Spider Mites 2 Days After Treatment

| Type | Formula Composition | Mean % Mortality |
|---|---|---|
| Tested comp. | 1.0% Triglycerides from canola oil, 55 ppm pyrethrins | 88.6 |
| Pyrethrum extract | 55 ppm Pyrethrins | 11.5 |
| Triglyceride control | 1.0% Triglycerides from canola oil (0 ppm pyrethrins) | 80.2 |
| Control | Distilled water | 4.5 |

EXAMPLE 3

Ants were aspirated into 16 dram plastic vials (5 ants per vial) which were then inverted onto 15.2 cm diameter Styrofoam plates, for each replicate. Before being treated, the ants were quickly banged out of the vial onto the plate. Treatments were then applied using a hand-held trigger sprayer (2 passes of spray over the plate per replicate). The ants were then immediately transferred to a paper towel lined, Styrofoam plate to remove excess solution. Using a fine brush, ants were transferred into filter paper lined petri dishes. Each petri dish contained a small pile of white sugar and a cotton roll moistened, to saturation point, with distilled water. A relatively high moisture level was maintained within the petri dish, after treatment, to avoid mortality from dehydration.

The tested arthropodicidal composition was derived from a concentrated formulation containing 94% by weight triglycerides from canola oil, 2% pyrethrum extract containing 25% active pyrethrins, and 4% CHEMAX T09. Prior to application the concentrate was diluted to contain 2.0% by weight triglycerides from canola oil and 0.01% active pyrethrins.

Mortality was assessed 72 hours later. The data obtained are shown below in Table 3.

TABLE 3

Mortality of Sugar Ants 3 Days After Treatment

| Type | Form. Conc. | Mean % Mortality | Expected Mean Mortality |
|---|---|---|---|
| Tested composition | 2.0% Triglycerides from canola oil, 0.01% pyrethrins | 95.0[1A] | 73.0 |
| Trounce ® | 1.0% F.A. Salts, 140 ppm pyrethrins | 68.0[A] | — |
| Pyrethrum extract | 0.01% Pyrethrins | 43.0[B] | — |
| Triglyceride control | 2.0% Triglycerides from canola oil (0 ppm pyrethrins) | 30.0[B] | — |
| Schultz Instant Insect Spray ® | 200 ppm Pyrethrins, 2000 ppm PBO | 100.0[A] | — |
| Schultz Instant Insect Spray ® | 1.0 ppm Pyrethrins, 10.0 ppm PBO | 13.0[BC] | — |

[1]Means followed by the same letter are not significantly different (P = 0.05; SNK). Data was converted prior to analysis using an arcsine transformation.

EXAMPLE 4

Ants were aspirated into 16 dram plastic vials (5 ants per vial) which were then inverted onto 15.2 cm diameter Styrofoam plates, for each replicate (8 replicates per treatment). Before being treated, the ants were quickly banged out of the vial onto the plate. Treatments were then applied using a hand-held trigger sprayer (2 passes of spray over the plate per replicate). The ants were then immediately transferred to a paper towel lined, Styrofoam plate to remove excess solution. Using a fine brush, ants were transferred into filter paper lined petri dishes. Each petri dish contained a small pile of white sugar and a cotton roll moistened, to saturation point, with distilled water. A relatively high moisture level was maintained within the petri dish, after treatment, to avoid mortality from dehydration.

The tested arthropodicidal composition was derived from a concentrated formulation containing 94% by weight triglycerides from canola oil, 2% pyrethrum extract containing 25% active pyrethrins, and 4% CHEMAX T09. Prior to application the concentrate was diluted to contain 2.0% by weight triglycerides from canola oil and 0.01% active pyrethrins.

Mortality was assessed 72 hours later and the data obtained are illustrated in Table 4.

TABLE 4

Mortality of Sugar Ants 3 Days After Treatment

| Type | Form. Conc. | Mean % Mortality | Expected Mean Mortality |
|---|---|---|---|
| Tested composition | 2.0% Triglycerides from canola oil, 0.01% pyrethrins | 95.0[1A] | 62.5[2S] |
| Trounce ® | 1.0% F.A. Salts, 140 ppm pyrethrins | 72.5[AB] | — |
| Control | Distilled water | 25.0[DE] | — |
| Pyrethrum extract | 0.01% Pyrethrins | 52.5[BC] | — |
| Triglyceride control | 2.0% Triglycerides from canola oil (no pyrethrins) | 10.0[DE] | — |
| Schultz Instant Insect Spray ® | 200 ppm Pyrethrins, 2000 ppm PBO | 97.5[A] | — |
| Schultz Instant Insect Spray ® | 110 ppm Pyrethrins, 1100 ppm PBO | 100.0[A] | — |

[1]Means followed by the same letter are not significantly different (P = 0.05; SNK). Data was converted prior to analysis using an arcsine transformation.
[2S]Synergy as determined by a two-tailed, two-sample t test (p = 0.05).

EXAMPLE 5

Late instar apple ermine moth larvae, *Yponomeuta malinellas*, were collected from apple trees in the field. Treatments consisted of 8 replicates of 5 insects each. Insects were sprayed to wetting, for every treatment, with the same hand-held trigger sprayer. After treatment, larvae were transferred to petri dishes containing a moistened filter paper and a piece of apple leaf.

The tested arthropodicidal composition was derived from a concentrated formulation containing 94% by weight triglycerides from canola oil, 2% pyrethrum extract containing 25% active pyrethrins, and 4% CHEMAX T09. Prior to application the concentrate was diluted to the concentration of active ingredients shown in Table 5.

Assessment was done after four days by counting the living and dead moth larvae and the data obtained is shown in Table 5.

TABLE 5

Mortality of Apple Ermine Moth Larvae 4 Days After Treatment

| Type | Formulation and Concentration | % Mortality | Expected Mean Mortality[1] |
|---|---|---|---|
| Oil control | 2.0% Triglycerides from canola oil (0 ppm pyrethrins) | 30.0[1C] | |
| Tested composition | 2.0% Triglycerides from canola oil, 0.01% pyrethrins | 100.0[A] | |
| Pyrethrum extract | 0.01% Pyrethrins | 97.5[A] | |
| Control | Distilled water | 2.5[D] | |
| Triglyceride control | 1.0% Triglycerides from canola oil (0 ppm pyrethrins) | 12.5[D] | |
| Tested composition | 1.0% Triglycerides from canola oil, 56 ppm pyrethrins | 100.0[A] | 62.5*[S] |
| Pyrethrum extract | 56 ppm Pyrethrins | 50.0[B] | |

[1] = Means followed by the same letter are not significantly different (P = 0.05; SNK).
*[S] = Synergy as determined by a two-tailed, two-sample t test (p = 0.05).

All concentrates referred to herein and expressed as percentages are percentages by weight of the composition unless otherwise stated.

EXAMPLE 6

The procedure of Example 5 was repeated using the same concentrated arthropodicidal composition described in Example 5, diluted to concentrations shown in Table 6. Assessment was done after four days by counting the living and dead moth larvae and the data obtained is shown in Table 6.

TABLE 6

Mortality of Ermine Moth Larvae Four Days After Treatment

| Type | Formulation and Concentration | % Mortality | Expected Mean Mortality |
|---|---|---|---|
| Triglyceride control | 1% Triglycerides from canola oil (0 pyrethrins) | 5.0 | |
| Pyrethrum extract | 56 ppm Pyrethrins | 35.0 | |
| Pyrethrum extract | 37 ppm Pyrethrins | 45.0 | |
| Pyrethrum extract | 19 ppm Pyrethrins | 17.5 | |
| Tested composition | 1% Triglycerides from canola oil, 56 ppm pyrethrins | 92.5 | 40.0*[S] |
| Tested composition | 1% Triglycerides from canola oil, 37 ppm pyrethrins | 92.5 | 50.0*[S] |
| Tested composition | 1% Triglycerides from canola oil, 19 ppm pyrethrins* | 60.0 | 22.5*[S] |
| Control | Distilled water | 0 | |

*[S] = Synergy as determined by a two-tailed, two-sample t test (p = 0.05)

All concentrates referred to herein and expressed as percentages are percentages by weight of the composition unless otherwise stated.

One of ordinary skill of the art will appreciate that minor modifications may be made in the compositions in the present invention without imparting from its intended scope.

What is claimed is:

1. A ready-to-use insecticidal composition, comprising:

approximately 20 to 4000 ppm of active pyrethrin substances selected from the group consisting of pyrethrin I and II, cinerin I and II, jasmolin I and II, and mixtures thereof;

approximately 1 to 5% by weight of a triglyceride component derived from vegetable seed oils selected from the group consisting of canola oil, cottonseed oil, soybean oil, sunflower oil, safflower oil, rape seed oil, peanut oil, olive oil, and mixtures thereof;

approximately 0.05 to 1.0% by weight of a nonionic surfactant selected from the group consisting of ethoxylated sorbitan derivatives, ethoxylated fatty acids, and mixtures thereof;

a gum component present at about 50 ppm to 0.1% by weight; and a balance of water, the composition being environmentally compatible and having little or no phytotoxicity.

2. The composition of claim 1 further comprising trace amounts of an antioxidant.

* * * * *

UNITED STATES PATENT AND TRADEMARK OFFICE
CERTIFICATE OF CORRECTION

PATENT NO. : 5,700,473  Page 1 of 2
DATED : December 23, 1997
INVENTOR(S) : George S. Puritch et al.

It is certified that error appears in the above-indentified patent and that said Letters Patent is hereby corrected as shown below:

TITLE PAGE

|  | Reads | Should read |
|---|---|---|
| Column 1,[75] Inventors: | Brentwood | Brentwood Bay |

Column 1,[56] References Cited:

| Document | Dated | Class/Subclass Should read |
|---|---|---|
| U.S. Patent 4,617,318 | 10/1986 | A01N 37/34 |
| U.S. Patent 4,983,591 | 1/1991 | A01N 37/00 |
| U.S. Patent 5,242,907 | 9/1993 | A01N 25/00 |
| French Patent 991628 | 4/1944 | 4 |

UNITED STATES PATENT AND TRADEMARK OFFICE
CERTIFICATE OF CORRECTION

PATENT NO. : 5,700,473
DATED : December 23, 1997
INVENTOR(S) : George S. Puritch et al.

It is certified that error appears in the above-indentified patent and that said Letters Patent is hereby corrected as shown below:

| Column | Line(s) | Reads | Should read |
|--------|---------|-------|-------------|
| 4 | 58 | mounts | amounts |
| 10 | 6 | rolI | roll |
| 10 | 30 (Table 4) | 95.0[1A] | 92.5[1A] |

Signed and Sealed this

Twenty-third Day of November, 1999

Attest:

Q. TODD DICKINSON

*Attesting Officer*      *Acting Commissioner of Patents and Trademarks*